United States Patent
Alberts

(10) Patent No.: US 6,732,013 B2
(45) Date of Patent: May 4, 2004

(54) METHOD AND APPARATUS FOR CHECKING PRODUCTS WITH LABELS

(75) Inventor: Petrus Antonius J. Alberts, Hengelo (NL)

(73) Assignee: Fountain Technologies, B.V., Cappele a/d IJssel (NL)

(*) Notice: Subject to any disclaimer, the term of this patent is extended or adjusted under 35 U.S.C. 154(b) by 0 days.

(21) Appl. No.: 10/187,421

(22) Filed: Jul. 1, 2002

(65) Prior Publication Data

US 2003/0000872 A1 Jan. 2, 2003

(30) Foreign Application Priority Data

Jun. 29, 2001 (NL) .............................. 1018427

(51) Int. Cl.[7] .............................................. G06F 7/00
(52) U.S. Cl. ...................................... 700/226; 700/223
(58) Field of Search ................................ 700/226, 223, 700/224; 198/346.2, 415; 382/141, 142, 143, 181

(56) References Cited

U.S. PATENT DOCUMENTS

| | | | | |
|---|---|---|---|---|
| 4,053,056 A | * | 10/1977 | Day ........................... | 209/587 |
| 4,414,566 A | * | 11/1983 | Peyton et al. ................ | 382/142 |
| 4,859,863 A | * | 8/1989 | Schrader et al. ............. | 250/556 |
| 4,872,084 A | * | 10/1989 | Dunning et al. ............. | 361/232 |
| 4,972,494 A | * | 11/1990 | White et al. ................. | 382/143 |
| 5,072,127 A | * | 12/1991 | Cochran et al. ........ | 250/559.39 |
| 5,189,708 A | * | 2/1993 | Cox et al. .................... | 382/143 |
| 5,245,399 A | * | 9/1993 | Wertz et al. .................. | 356/71 |
| 5,256,365 A | * | 10/1993 | Gordon et al. .............. | 264/509 |
| 5,991,018 A | * | 11/1999 | Imaizumi et al. ......... | 356/239.1 |
| 6,199,679 B1 | * | 3/2001 | Heuft .......................... | 198/415 |

* cited by examiner

Primary Examiner—Gene O. Crawford
(74) Attorney, Agent, or Firm—Hoffmann & Baron, LLP

(57) ABSTRACT

A method for checking products with labels, wherein:
 a product is formed and is provided on one side, in particular an outer side, with a label which, at least in fitted condition, forms at least one closed surface;
 the product is brought between a light source and a light-sensitive device; and
 with the light-sensitive device, the pattern and/or intensity of light originating from the light source and falling through the product, in particular through and/or alongside the label, is measured;
 wherein the light-sensitive device produces a rejection signal if the pattern and/or the intensity do not agree with a pre-set pattern and/or intensity.

23 Claims, 3 Drawing Sheets

METHOD AND APPARATUS FOR CHECKING PRODUCTS WITH LABELS

BACKGROUND OF THE INVENTION

The present invention relates to a method for checking products with labels.

It is known to provide products with decorations by providing labels thereon. These labels may be adhered to the inside or outside of a product or, preferably, are provided by in-mold labeling technique. These labels moreover, besides providing the decoration, typically afford protection of goods to be packaged in the products, for instance from the influence of light. In this connection it is highly important for the labels to be fitted in the correct manner. In substantially rectangular holder-shaped products, often labels are used that in flat condition have roughly the shape of a Maltese cross, that is, a central surface having four adjoining cross surfaces. The central surface is then placed against the bottom of the holder, the cross surfaces against the four side surfaces of the holder. The cross surfaces must adjoin each other accurately along the ribs of adjacent side surfaces, such that no light can pass between these surfaces and, moreover, any decorations continue across the ribs. If this has been achieved to an insufficient extent, the products are rejected.

Commonly, products are inspected visually. To that end, the products in a production line are looked at by quality inspectors, who remove poorly labeled products from the production line. In more advanced methods, cameras with pattern recognition means are used. The labels are then provided with printings recognizable to the pattern recognition means, which printings can be compared with pre-inputted patterns. In case of insufficient agreement, the product involved is removed. These known methods have the drawback that they are particularly labor-intensive and moreover lead to an undesirably high percentage of errors. In the known method, the use of the pattern recognition means moreover leads to the drawback that only specific patterns are recognizable. Furthermore, for this purpose, a relatively large number of cameras must be used, which is costly and involves susceptibility to trouble.

The invention has for its object to provide a method of the type described in the opening paragraph, in which the above drawbacks of the known methods are avoided, while retaining the advantages thereof. To that end, a method according to the invention is characterized by the measures according to claim 1.

SUMMARY OF THE INVENTION

In a method according to the invention, use is made of a light source and light-sensitive means to trace any errors in a product with a label. It has been found that with a method according to the invention errors can be traced particularly fast and accurately. In the method, moreover, use can be made of simple light-sensitive means. Especially if use is made of both measurement of light falling through and of pattern recognition, a particularly high accuracy can be achieved. Moreover, by means of a rejection signal other parts of the same or a different apparatus may be controlled, for instance discharge means for rejected products or means for positioning the labels. Thus, an optimally automated method can be obtained for manufacturing and checking products with labels.

The invention further relates to an apparatus for checking products with labels. According to the invention, such an apparatus is characterized by the features according to claim 7.

In an apparatus according to the invention, use is made of a light source and light-sensitive means to trace any errors in a product with a label. It has been found that with an apparatus according to the invention errors can be traced very fast and accurately and use can be made of simple light-sensitive means. Especially if use is made of both measurement of light falling through and pattern recognition, a particularly high accuracy can be achieved. Moreover, by means of a rejection signal, other parts of the same or a different apparatus may be controlled, for instance discharge means for rejected products or means for positioning the labels.

An apparatus according to the invention is particularly suitable for checking in-mold labeled injection molded products to be used as packages, with both the bottom and the longitudinal walls labeled, and the labels having edge portions adjoining each other, in particular adjacent the ribs of the holder. An apparatus according to the invention is preferably provided with a table having an opening against which or over which the holder can be placed by an open side thereof, the table being provided with an abutment edge around the opening to provide a substantially light-tight seal between the holder and the table. Thus, the desired light-tightness of the holder can be checked particularly fast.

An apparatus according to the invention is preferably provided with a discharge device controlled on the basis of the presence or absence of a rejection signal for a respective product. Thus, products can be automatically conveyed further for later use or be discharged if the labels have not been provided in the correct manner or if other defects are established. The products are preferably supplied by means of belt conveyer means and picked up and displaced within the apparatus with the aid of suction means, at least reduced pressure means, such as suction cups, or the like. By these means, the products can be picked up and displaced simply, rapidly, and accurately, without damage.

An apparatus according to the invention is preferably of such design that at least two products can be handled simultaneously, in particular can be checked simultaneously. Also, the apparatus may be of such design that in each case two juxtaposed feeding and discharge means make use of a checking apparatus disposed between them and comprising the at least one light source and light-sensitive device. Furthermore, it is then preferred that the apparatus be of modular construction, such that it can be easily and rapidly adapted to other types of products.

Further advantageous embodiments of an apparatus and a method according to the invention are described in the subclaims.

BRIEF DESCRIPTION OF THE DRAWINGS

To clarify the invention, exemplary embodiments of an apparatus and a method according to the invention will be elucidated in more detail with reference to the drawing. In the drawing.

DETAILED DESCRIPTION OF THE PREFERRED EMBODIMENTS

Figure 1:
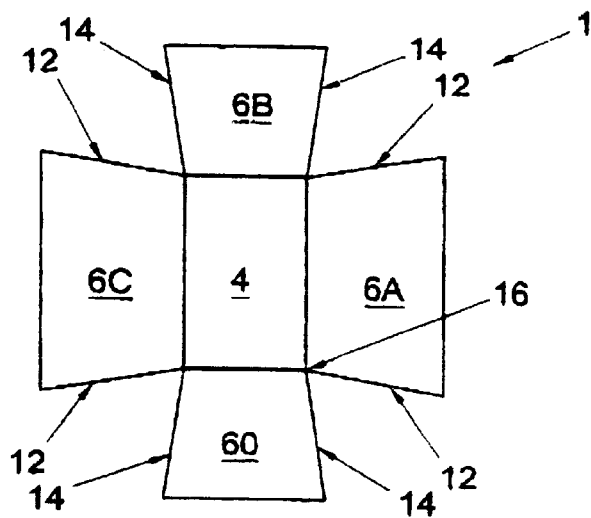
FIG. 1 shows a label in flat condition.

In this description, the same or corresponding parts have the same or corresponding reference numerals. In this description, by way of example, a holder, for instance a tub of butter, with a label is shown. It will be clear, however, that all kinds of other products can also be checked in the same manner.

Figure 2:
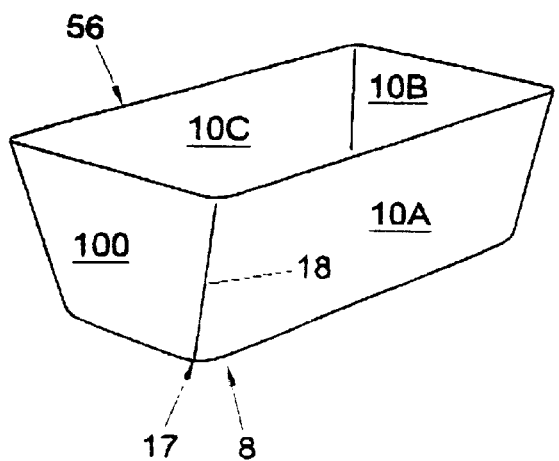
FIG. 2 diagrammatically shows, in perspective elevation, a holder provided with a label according to FIG. 1.

FIG. 1 shows, in flat condition, a label 1 for use on a holder 2 as shown in FIG. 2. The label 1 comprises a substantially rectangular central surface 4 and four cross surfaces 6a–d extending therefrom, so that the label 1 is somewhat in the shape of a Maltese cross. The holder 2 comprises a bottom surface 8 and four side walls 10a–d, to some extent diverging from the bottom 8. The label 1 may, for instance, be provided on one side with an adhesive layer and be adhered to the holder 2, with the central surface 4 being adhered to the bottom 8 of the holder and the cross surfaces 6a–d being adhered to the respective side walls 10a–10d. Preferably, however, the label 1 is provided in a mold cavity (not shown), after which the holder 2 is injection molded against the label, in a known manner with in-mold labeling technique, so that an integral connection is obtained between the label 1 and the holder 2.

The cross surface 6a has a side edge 12, the cross surface 6d has a side edge 14, which side edges 12, 14 meet in an angular point 16 of the central surface 4.

Figure 3:
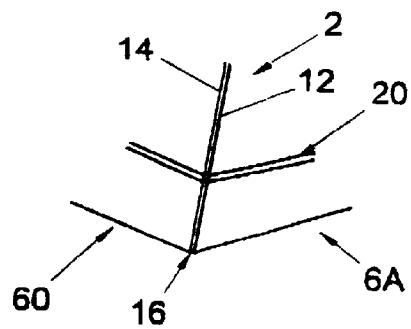
FIG. 3 diagrammatically shows, in perspective elevation, a portion of a label fitted in the right condition.
Figure 6:
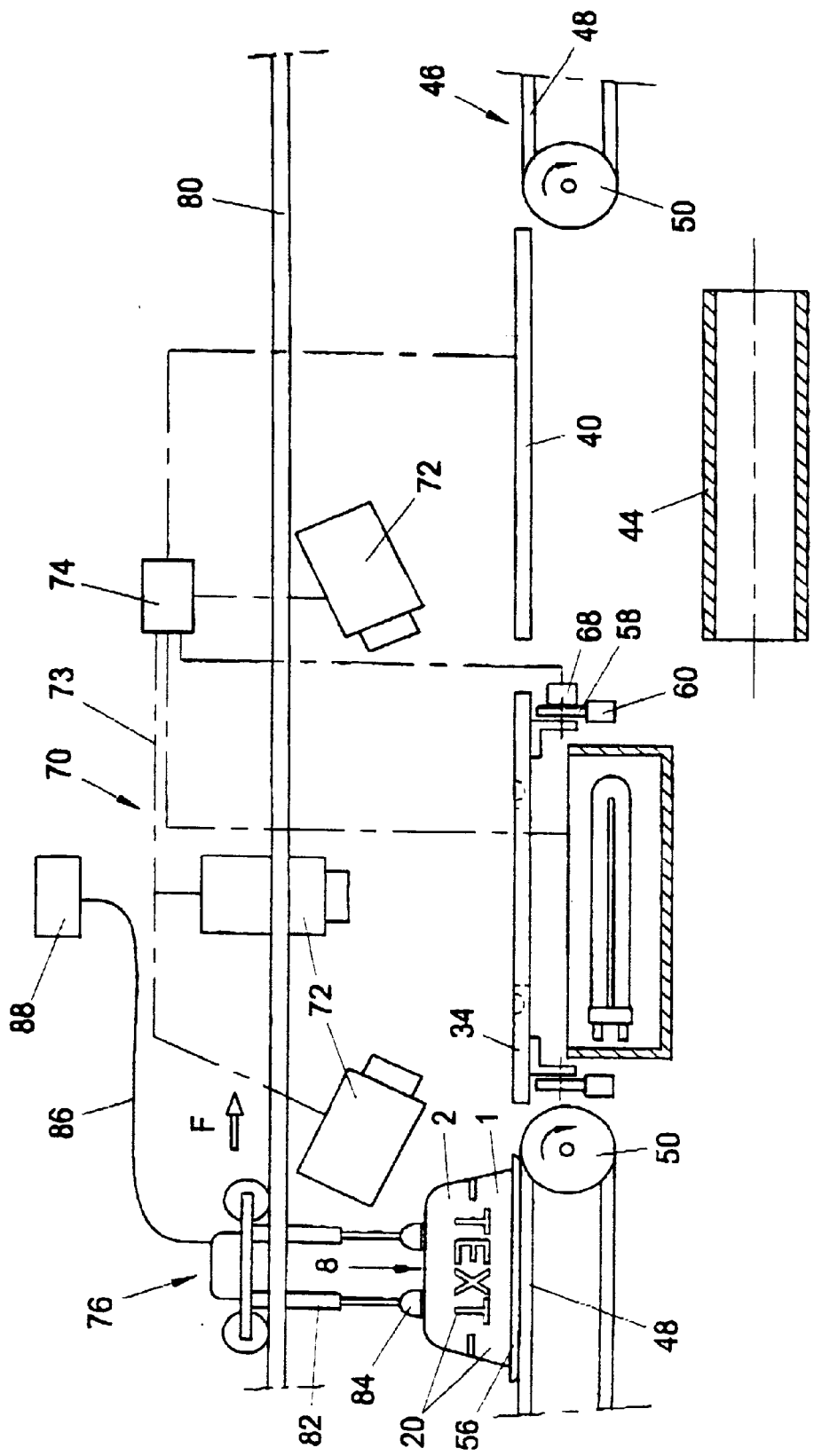
FIG. 6 diagrammatically shows, in side elevation, an apparatus according to FIG. 5.

FIG. 3 shows, in perspective elevation, a corner of the holder 2 with a label 1 provided thereon, with the angular point 16 coinciding with a corner 17 of the holder 2. The cross surfaces 6a, 6d are folded against the side walls 10a, 10d, such that the longitudinal edges 12, 14 of the respective side surfaces 6a, 6b touch each other along the ribs 18. In a comparable manner, the other cross surfaces 6b, 6c are folded against the respective side walls 10b, 10c, so that the longitudinal edges 12, 14 thereof lie against each other. The rib 18 is thus no longer visible. Provided on the outer sides of the label 1 is a printing 20, for instance lines or text (FIG. 6). In the embodiment shown in FIG. 3, this printing 20 continues across the ribs 18 from one cross surface 6a to the adjacent cross surface 6d. If the label 1 has been fitted correctly, as shown in FIG. 3, for instance a continuous pattern 20 is thus obtained.

Figure 4:
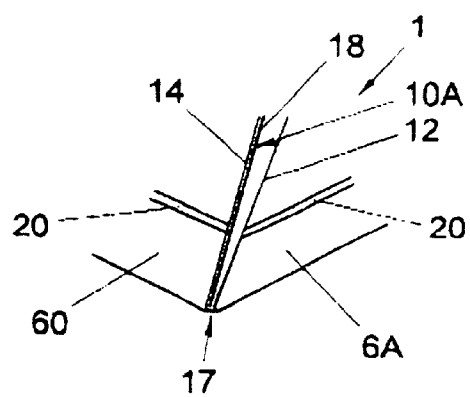
FIG. 4 diagrammatically shows, in perspective elevation, a portion of an incorrectly fitted label.

FIG. 4 shows the same corner 17 of the holder, on which, however, the label 1 has been provided incorrectly. Visible between the side edge 14 of the cross surface 6d and the side wall 12 of the cross surface 6a is the rib 18 as well as an uncovered part of the side wall 10a. The printing 20, in particular the lines, do not continue across the rib 18, so that an unwanted pattern is obtained. The position of the label 1 on the holder 2 can be checked with an apparatus according to the invention, as shown in FIGS. 5 and 6.

Figure 5:
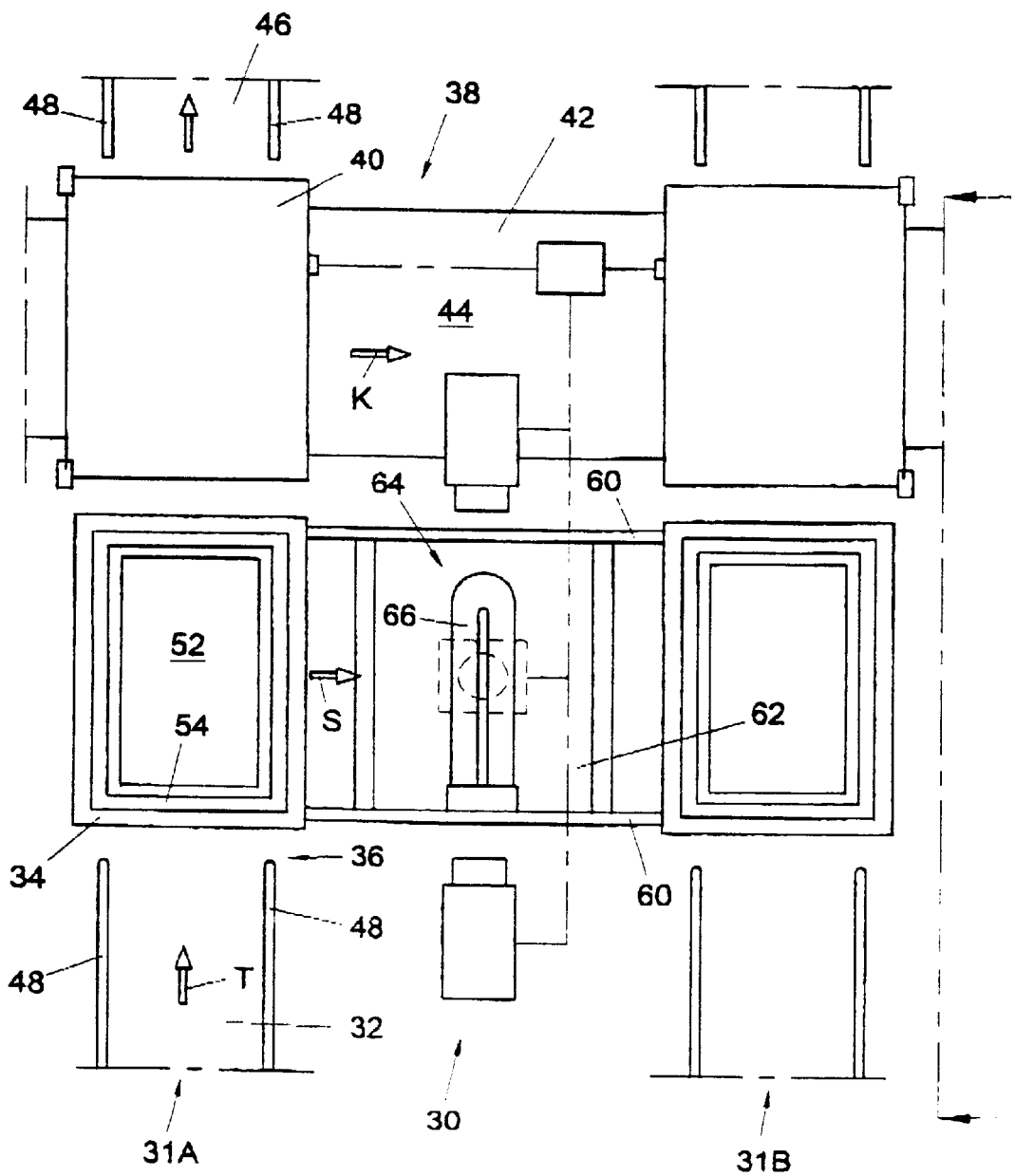
FIG. 5 diagrammatically shows, in top plan view, an apparatus according to the invention.

The apparatus 30 according to the invention is shown in part in FIG. 5, comprising two feed-through paths 31a, 31b for feeding through products, such as the holder 2 as shown in FIGS. 1–4. For clarity's sake, the holders 2 are omitted in FIG. 5, whilst the apparatus 30 is shown diagrammatically of the apparatus 30, specifically the left-hand path 31a will be described. The right-hand path 31B is substantially identical thereto.

The apparatus 30 comprises first feeding means 32, a table 34 linking up with the leading end 36 of the first feeding means 32, as well as discharge means 38, comprising a valve 40, arranged on the side of the table 34 remote from the first feeding means 32, and conveying means 42 placed therebelow, in particular a conveyor belt 44. The first feeding means 32 have a conveying direction T in the direction of the table 34, the conveyor belt 44 has a conveying direction K approximately at right angles to the conveying direction T. Connected on the side of the valve 40 remote from the table 34 are second discharge means 46. In this embodiment, the first feeding mean 32 and the second discharge means 46 are designed as two circular conveyor belts 48 extending side by side, on which holders 2 can be supported. The holders 2, as shown in FIG. 6, are arranged upside down, that is, with the bottom 8 directed upwards, remote from the belt 48. The belt elements 48 have been passed around guide wheels 50.

The table 34 is centrally provided with an opening 52, around which extends a groove 54 in which a longitudinal edge 56 of the holder 2 can be received with a proper fit, such that a substantially light-tight seal is obtained between the groove 54, at least the table 84, and the longitudinal edge 56. The holder 2 shown in FIG. 6 has an outwardly bent longitudinal edge 56, as known, for instance, in tubs of (low-fat) margarine, on which longitudinal edge 56 a lid (not shown) can be placed. In FIG. 2 this edge is omitted, for clarity's sake.

The table 34 is placed on rails 60 by way of rollers 58, such that the table 34 can be rolled in a direction S, at right angles to the conveying direction T. Provided between the tables 34 in the paths 31a, 31b, between the rails 60, is a light box 62, which is shown in FIG. 6 in sectional view. Included in the light box 62 is a light source 64, for instance a tubular lamp 66. In FIG. 6 the distance between the underside of the table 34 and the light box 62 is represented as being relatively large. In reality, the table 34 will preferably move closely above the light box 62. During use, the table 34 can be moved with the opening 52 above the tubular lamp 66, for instance by driving one of the rollers 58 with a motor 68, such that light from the light source 64 can reach through the opening 52 into the inner space of a holder 2 supported on the table 34. Light from the light source 64 will fall through the side walls 10 and the bottom 8 of the holder 2 and in some measure through the label 1. There will be a difference between the light falling through parts of the holder 2 covered by the label 1 and parts not covered by the label 1. Especially relevant here is the difference in light falling through correctly fitted labels 1, as shown in FIG. 3, in particular between the longitudinal edges 12 and 14, and incorrectly fitted labels, as shown in FIG. 4, so that space exists between the longitudinal edges 12, 14, and light shines through the uncovered part of the side wall 10a. Provided between the paths 31a, 31b is a light-sensitive device 70, in the embodiment shown in the form of three cameras 72. It is also possible to use different numbers of cameras, possibly just one camera centrally above the light box 62. The cameras are connected via suitable cable work 73 to a central control unit 74, with which, in a manner to be described hereinafter, inter alia the valve 40 can be controlled, as well as the table 34 and transport means 76, with which a holder 2 can be picked up and placed on the table or can be picked up from the table and placed on the valve 40 or the second discharge means 46, depending on signals to be described hereinafter.

With the light-sensitive device 70, during use, a holder 2 placed between the light source 64 and the light-sensitive device 70 can be checked, whereby light from the light source 64 shining through the holder can be observed, yielding an image which can be compared by means of the control unit 74 with a previously inputted image or pattern matching a holder 2 of the subject type on which the label 1 has been fitted correctly, as shown, for instance, in FIG. 3.

Moreover, permissible tolerances may be inputted in the control unit 74, for instance a quantity of light failing between longitudinal edges 12, 14 that is considered permissible. In the event of a deviation from the desired image that is greater than is considered permissible, the control unit 74 produces a signal which can be designated as rejection signal. With this signal, the valve 40 can be controlled. This valve can be opened on the basis of a rejection signal, such that a rejected holder 2, that is, a holder whose image observed by the light-sensitive device 70 deviates unduly from the desired image, can pass the valve and be received in the discharge device 38, so that it can be carried off by the belt 44, for instance for recycling.

Provided above each path 31a, 31b is a transfer device 76 supported by guide rails 80 extending in the conveying direction T. The transfer device 76 carries piston-cylinder assemblies 82 provided with suction cups 84 which, by means of the piston-cylinder assemblies 82, can be placed against the product 2, in particular the bottom 8, whereupon a reduced pressure can be generated in the suction cups 84 to pick up the holder 2. To that end, the piston-cylinder assemblies 82 and the suction cups 84 are connected via a line 86 with a pneumatic device 88. After the holder 2 in the position shown in FIG. 6 has been seized with the suction cups 84, it can be lifted from the feeding means 32 and be transferred to the table 34 with the transfer device 76. There the holder 2 will be released and with the table 34 be moved in the direction S to above the tubular lamp 66. In that position, the tubular lamp 66 is switched on, and with the light-sensitive device 70 an image of light passing through the holder 2, in particular through and alongside the label 1, is recorded and transmitted to the central control unit 74, in which the image is compared with the desired image. Next, the table 34 with the holder 2 is moved back into the path 31a, where the holder 2 is picked up again with the transfer device 76 and is moved further in the direction T, at least to above the valve 40. If on the basis of this holder 2 a rejection signal has been produced by the central control unit 74, the valve 40 is controlled to open and the holder 2 is released above the thus created opening, so that it falls onto the belt 44 and can be carried off for recycling. If on the basis of this holder 2 no rejection signal is produced, or possibly an acceptance signal, then the holder 2 is moved further by means of the transfer device 76 to above the second discharge means 46 and set down thereon, so that the holder 2 can be passed further for further processing, for instance to be filled, at least stacked for further use. It will be clear, for that matter, that cracks or other imperfections in the label 1 can also be observed with an apparatus according to the invention.

It is preferred that with the light-sensitive device 72 not only an image of transmitted light is formed, but also that by means of pattern recognition the labeling is examined and is compared with a desired labeling image. Thus the printing of the label 1 can be checked as well, as a second check. If the correct printing, at least the correct condition of the printing, has not been obtained, likewise a rejection signal can be produced, with the consequences described earlier.

It is preferred that at least two transfer devices 76 are provided, one after the other in the conveying direction T, with which at the same time a holder 2 can be picked up from the first feeding means 32 and a holder 2 can be picked up from the table 34 and the two holders can be moved at the same time, one to the table 34 and the other to the valve 40 or the second discharge means 46, depending on the presence or absence of the rejection signal. Thus, a large number of holders can be checked still faster.

The invention is by no means limited to the exemplary embodiments shown in the description and the drawing. Many variations thereof are possible within the scope of the invention outlined by the claims.

For instance, the discharge device may be designed in many ways, with the valve 40 possibly omitted. For instance, in the event of a rejection signal, holders may be blown away from the second discharge means or be put away beside the second discharge means in a different manner. In the condition shown in FIG. 5, two paths 31a, b are shown, allowing the table 34 of the left-hand path 31a and the table of the right-hand path 31b to be alternately moved above the light source 64 for alternately testing holders. However, it is, of course, also possible for each path 31 to be provided with a light source. Also, the light source 64 could be arranged directly below the path 31, in which case, however, a different arrangement of the light-sensitive device 70 is to be chosen to avoid collision of the transfer device 76 and the light-sensitive device 70. Also, holders 2 may, for instance, be moved over the light box 62 directly with a belt conveyor, such as the first feeding means 32, so that the holders can be moved directly between the light source and the light-sensitive device. Additionally, for instance the light box, at least the light source, may be arranged for movement in vertical direction, so that it can be moved closely below or even into the holder. Furthermore, the light source may be placed above and the light-sensitive device below the path, or on opposite sides thereof, while the position of the tested products may be simply adjusted. It will be clear that with an apparatus according to the invention, also differently shaped products, for instance flat products, may be tested, in all of which cases a desired image can be stored in the control unit 74 for comparison with a current observed image.

These and many comparable variations are understood to fall within the scope of the invention outlined by the claims.

What is claimed is:

1. A method for checking products with labels, comprising:

forming a product having on at least one side, in particular an outer side, a label which, at least in fitted condition, forms at least one closed surface;

placing the product between a light source and a light-sensitive device;

shining light from said light source through the product;

measuring with the light-sensitive device, the pattern and/or intensity of light originating from said light source and falling through the product, in particular through and/or alongside the label;

producing a rejection signal with said light-sensitive device if said pattern and/or said intensity do not agree with a pre-set pattern and/or intensity.

2. A method according to claim 1, wherein the product is holder-shaped and said at least one label is connected by in-mold labeling technique.

3. A method according to claim 1, further comprising the steps of:

moving the product over the light source, and wherein the light-sensitive device is at least one camera, and comparing at least one pattern of light from the light source falling through openings in the label with a comparative pattern stored in the light-sensitive device.

4. A method according to claim 1, further comprising the steps of:

feeding and discharging the products in a first direction, moving the products out of the product stream in a lateral direction with respect to said first direction to a position between said light source and said light-sensitive device, and returning the products to the product stream after measurement.

5. A method according to claim 1, further including the step of energizing a discharge device for leading the respective product out of a product stream, in particular to a recycling unit on the basis of said rejection signal.

6. A method according to claim 5, further including the step of providing said discharge device with at least one valve, which, in closed condition, allows said product stream to pass and, on the basis of said rejection signal, is controlled to open, such that said product on the basis of which said rejection signal has been produced, falls out o the product stream, after which the at least one valve is controlled to close again.

7. A method according to claim 1, wherein said product includes a bottom and longitudinal walls extending therefrom to form an open side and said label having edge portions adjoining each other.

8. A method according to claim 7, further including the steps of:

placing said open said of said product over said light source; and positioning said light-sensitive device on the opposite side of said product to measure the pattern and/or intensity of light falling through the product and label.

9. An apparatus for checking products with labels, comprising:

feeding means for feeding products provided on at least one side, in particular an outer side, with a label which, at least in fitted condition, forms at least one closed surface;

a light source and a light sensitive device, as well as positioning means for positioning a product between the light source and the light-sensitive device; and recognition means for comparing a pattern of light originating from said light source and falling through the product, in particular through and/or alongside the label, measured with the light-sensitive device, with a reference pattern stored in the recognition means;

wherein signaling means are provided for producing a rejection signal if said pattern does not agree with a pre-set pattern.

10. An apparatus according to claim 9, wherein the feeding means comprise suction means for picking up products.

11. An apparatus according to claim 9, wherein the feeding means comprise belt-shaped conveying means which connect to the positioning means and can support the products.

12. An apparatus according to claim 9, wherein the feeding means are provided for simultaneously checking at least two products.

13. An apparatus according to claim 9, wherein a discharge device is provided, controllable on the basis of said rejection signal, between a first position in which a product can pass the discharge device if no rejection signal is produced and a second position in which a product is received in the discharge device if a rejection signal is produced.

14. An apparatus according to claim 13, wherein the discharge device comprises at least one valve, movable between a first closed position and a second open position; wherein a product is movable from a set-up position over the valve when the valve is in the first position or along the valve into the discharge device when the valve is in the second position.

15. An apparatus according to claim 14, wherein suction means are provided for displacing a product to above or beyond said valve, depending on said rejection signal.

16. An apparatus according to claim 9, wherein the positioning means comprise at least one movable table for bringing the products between the light source and the light-sensitive device.

17. An apparatus according to claim 9, wherein the table comprises at least one opening, as well as abutment means surrounding said at least one opening for sealing abutment against a product, such that during use light from the light source falling through the at least one opening can reach the light-sensitive device only through said product.

18. An apparatus according to claim 17, wherein said product comprises:

a bottom; and at least one longitudinal wall extending from said bottom and terminating at a longitudinal edge forming an open end opposite said bottom, said at least one longitudinal wall adjoining itself or another wall to form a ridge, and wherein said label attached to said product having edge portions adjoining each other.

19. An apparatus according to claim 18, wherein said light source is positioned below said at least one opening to shine light through said product, wherein said abutment means forms a light-tight seal between said table and said longitudinal edge of said product, and said light-sensitive device is a camera positioned on the opposite side of the product than said light source.

20. An apparatus for checking products with labels, comprising:

a suction means for picking up a product, said product provided on at least one side, in particular an outer side, with a label which, at least in fitted condition, forms at least one closed surface;

a light source and a light-sensitive device, as well as positioning means for positioning said product between the light source and the light-sensitive device; and recognition means for comparing a pattern of light originating from said light source and falling through said product, in particular through and/or alongside the label, measured with the light-sensitive device, with a reference pattern stored in the recognition means;

wherein signaling means are provided for producing a rejection signal if said pattern does not agree with a pre-set pattern.

21. An apparatus for checking products with labels, comprising:

feeding means for feeding products provided on at least one side, in particular an outer side, with a label which, at least in fitted condition, forms at least one closed surface;

a light source and a light-sensitive device, as well as positioning means, said positioning means having at least one moveable table for positioning a product between the light source and the light-sensitive device; and recognition means for comparing a pattern of light originating from said light source and falling through the product, in particular through and/or alongside the label, measured with the light-sensitive device, with a reference pattern stored in the recognition means;

wherein signaling means are provided for producing a rejection signal if said pattern does not agree with a pre-set pattern.

22. An apparatus for checking products with labels, comprising:

feeding means for feeding products provided on at least one side, in particular an outer side, with a label which, at least in fitted condition, forms at least one closed surface;

a light source and a light-sensitive device, as well as positioning means, said positioning means having at least one moveable table for positioning a product between the light source and the light-sensitive device, wherein said table comprises at least one opening, as well as abutment means surrounding said at least one opening for sealing abutment against said product, such that during use light from the light source falling through the at least one opening can reach the light-sensitive device only through said product; and recognition means for comparing a pattern of light originating from said light source and falling through the product, in particular through and/or alongside the label, measured with the light-sensitive device, with a reference pattern stored in the recognition means;

wherein signaling means are provided for producing a rejection signal if said pattern does not agree with a pre-set pattern.

23. An apparatus for checking products with labels, comprising:

feeding means for feeding products provided on at least one side, in particular an outer side, with a label which, at least in fitted condition, forms at least one closed surface;

a light source and a light-sensitive device, as well as positioning means for positioning a product between the light source and the light-sensitive device;

recognition means for comparing a pattern of light originating from said light source and falling through the product, in particular through and/or alongside the label, measured with the light-sensitive device, with a reference pattern stored in the recognition means;

wherein signaling means are provided for producing a rejection signal if said pattern does not agree with a pre-set pattern;

a discharge device having at least one valve, said at least one valve having a first closed position and a second open position, said discharge device is controllable on the basis of said rejection signal, wherein if no rejection signal is detected said product is movable from a set-up position over said at least one valve and passes said discharge device when said at least one valve is in said first position, and if a rejection signal is detected said product is movable along said at least one valve into said discharge device when said at least one valve is in said second position; and a suction means for displacing said product above or beyond said at least one valve depending on said rejection signal.

\* \* \* \* \*

UNITED STATES PATENT AND TRADEMARK OFFICE
CERTIFICATE OF CORRECTION

PATENT NO. : 6,732,013 B2
DATED : May 4, 2004
INVENTOR(S) : Alberts

It is certified that error appears in the above-identified patent and that said Letters Patent is hereby corrected as shown below:

Title page,
Item [57], ABSTRACT, now reads:
"A method for checking products with labels, wherein:
a product is formed and is provided on one side, in particular an outer side, with a label which, at least in fitted condition, forms at least one closed surface;
the product is brought between a light source and a light-sensitive device; and
with the light-sensitive device, the pattern and/or intensity of light originating from the light
source and falling through the product, in particular through and/or alongside the label, is measured;
wherein the light-sensitive device produces a rejection signal if the pattern and/or the intensity do not agree with a pre-set pattern and/or intensity."
should read:
-- The present invention relates to a method for checking products with labels. A product having a label on one surface is brought between a light source and a light sensitive device. The light source shines a light through the surface having the label. The light sensitive device detects the intensity of the light pattern and/or intensity of the light originating from the light source and falling through the label. The pattern of light that passes through the label or alongside the label is measured and compared to a predetermined pattern or intensity value. A rejection signal is produced depending on the measured value as compared to the predetermined value. --

Column 4,
Line 17, now reads "table 84" should read -- 34 --

Column 5,
Line 2, now reads "light failing" should read -- light falling --

Signed and Sealed this

Seventeenth Day of August, 2004

JON W. DUDAS
*Acting Director of the United States Patent and Trademark Office*